(12) United States Patent
Hauck et al.

(10) Patent No.: US 6,395,178 B1
(45) Date of Patent: May 28, 2002

(54) THIN POROUS LAYERS FOR THIN-LAYER CHROMATOGRAPHY

(75) Inventors: Heinz-Emil Hauck, Gross-Umstadt; Rolf Eymann; Günther Sättler, both of Reinheim, all of (DE)

(73) Assignee: Merck Patent Gesellschaft mit beschrankter Haftung, Darmstadt (DE)

(*) Notice: Subject to any disclaimer, the term of this patent is extended or adjusted under 35 U.S.C. 154(b) by 0 days.

(21) Appl. No.: 09/601,617

(22) PCT Filed: Jan. 19, 1999

(86) PCT No.: PCT/EP99/00284
§ 371 (c)(1),
(2), (4) Date: Aug. 4, 2000

(87) PCT Pub. No.: WO99/41602
PCT Pub. Date: Aug. 19, 1999

(30) Foreign Application Priority Data

Feb. 11, 1998 (DE) .......................................... 198 05 395

(51) Int. Cl.$^7$ ................................................ B01D 15/08
(52) U.S. Cl. .................... 210/635; 210/658; 210/198.3; 210/502.1; 436/162; 502/402; 502/439
(58) Field of Search ................................ 210/635, 656, 210/658, 198.3, 502.1; 422/70; 436/162; 502/401, 402, 408, 439

(56) References Cited

U.S. PATENT DOCUMENTS

| | | | | | |
|---|---|---|---|---|---|
| 4,095,950 A | * | 6/1978 | Kahn | ........................ | 210/198.3 |
| 4,276,061 A | * | 6/1981 | Nestrick | .................. | 210/198.3 |
| 4,295,968 A | * | 10/1981 | Halpaap | ................... | 210/198.3 |
| 4,741,830 A | * | 5/1988 | Hauck | ....................... | 210/198.3 |
| 4,793,921 A | * | 12/1988 | Hauck | ....................... | 210/198.3 |
| 5,882,939 A | * | 3/1999 | Kovar | ....................... | 210/198.3 |
| 5,935,862 A | * | 8/1999 | Novak | ......................... | 436/162 |

FOREIGN PATENT DOCUMENTS

| | | | | |
|---|---|---|---|---|
| DE | 1943304 | 4/1970 | .............. | 210/198.2 |
| DE | 2155281 | 5/1973 | .............. | 210/198.2 |
| DE | 2809137 | 9/1979 | .............. | 210/198.2 |
| DE | 3524357 | 1/1986 | .............. | 210/198.2 |
| DE | 19509949 | 9/1996 | .............. | 210/198.2 |
| EP | 0170143 | 2/1986 | .............. | 210/198.2 |

* cited by examiner

Primary Examiner—Ernest G. Therkorn
(74) Attorney, Agent, or Firm—Millen, White, Zelano & Branigan, P.C.

(57) ABSTRACT

Novel separation materials for thin layer chromatography are disclosed; these consist of a support and a separation medium layer and are obtainable by the following process steps:

a) cleaning of the support;
b) application of a liquid film comprising a polysilicic ester to a support;
c) introduction of the support with the liquid film into an atmosphere which effects hydrolysis and further polymerization of the polysilicic ester;
d) hydrolysis and further polymerization of the polysilicic ester at constant temperature;
e) washing of the silica layer;
f) drying of the silica layer.

The silica gel surface of the separation material of the invention can be modified by means of separation effectors.

7 Claims, 1 Drawing Sheet

THIN POROUS LAYERS FOR THIN-LAYER CHROMATOGRAPHY

REFERENCE TO RELATED APPLICATIONS

This application is a 371 of PCT/EP99/00284 filed Jan. 19, 1999.

The invention relates to separation materials for planar chromatography which have porous separation medium layers of low thickness and are suitable for the separation of substances on the nL scale.

Increasing demands made of the performance of analytical methods, in particular in respect of speed and detection sensitivity, mean that in the case of thin layer chromatography (planar chromatography) there is a need for separation medium layers which are significantly thinner than those obtainable hitherto, i.e. thinner than 50 μm.

Cremer and Nau (1968) describe experiments (Naturwissenschaften 55, page 651) in which chromatographic separations were carried out on ultrathin layers. The layers used consisted of indium oxide, bismuth oxide or tin oxide and had a thickness of 1 μm or less. These layers were vapour-deposited. The substances were able to be separated on model systems, but the method has not found further use. For thin layer chromatography, the practice has thus hitherto been to apply particulate separation media, which can have spherical or irregular shapes, to a support. In this procedure, it is possible to add auxiliaries such as binders, fluorescent indicators, reflection reinforcers or the like to the layer. Such additives are well known to those skilled in the art. In this method, it does not appear to be possible to reduce the thickness of the separation medium layer to less than 50 μm.

It has been found that significantly thinner separation medium layers, for example layers having a thickness of about 10 μm, can be produced using a completely different principle which has hitherto not been customary for the production of separation medium layers of silica gel for thin layer chromatography.

These processes and the separation materials for thin layer chromatography produced by means of these processes are provided by the present invention.

DE 19 08 695 discloses methods of applying thin coherent films of titanium dioxide and/or zirconium dioxide having a thickness of less than 1 μm to plastic films. This is said to prevent impurities from the plastic getting into the separation medium layer. However, these layers of titanium dioxide and/or zirconium dioxide have no chromatographic activity.

The invention provides separation materials for thin layer chromatography consisting of a support and a separation medium layer obtainable by the following process steps:
 a) cleaning of the support;
 b) application of a liquid film comprising a polysilicic ester to a support;
 c) introduction of the support with the liquid film into an atmosphere which effects hydrolysis and further polymerization of the polysilicic ester;
 d) hydrolysis and further polymerization of the polysilicic ester at constant temperature;
 e) washing of the silica layer;
 f) drying of the silica layer.

The invention further provides separation materials having the features mentioned, whose silica gel surface is modified by means of separation effectors.

The invention also provides for the use of separation materials having the features mentioned for separation of at least two substances by thin layer chromatography.

Finally, the invention provides a process for producing separation materials, which comprises the following steps:
 a) cleaning of the support;
 b) application of a liquid film comprising a polysilicic ester to a support;
 c) introduction of the support with the liquid film into an atmosphere which effects hydrolysis and further polymerization of the polysilicic ester;
 d) hydrolysis and further polymerization of the polysilicic ester at constant temperature;
 e) washing of the silica layer;
 f) drying of the silica layer;
where, in preferred embodiments, the process step b) is carried out by spraying the solution onto the support or the liquid film is applied by firstly applying the liquid at one point and subsequently rotating the support around the point of application, with the axis of rotation perpendicular to the plane of the support, or by distributing the liquid film using a roller.

DESCRIPTION OF THE PREFERRED EMBODIMENTS

Figure 1:
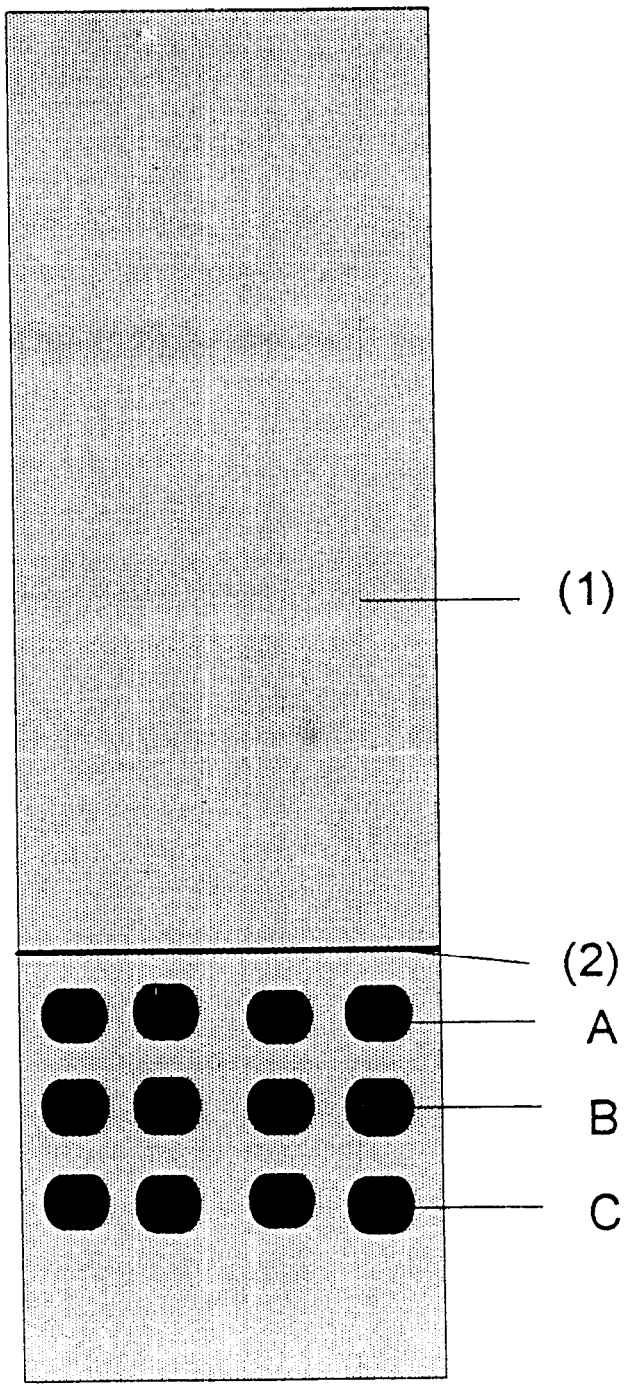
FIG. 1 schematically shows the separation of a dye mixture.

FIG. 1 schematically shows, in enlarged form, the separation of a dye mixture. The separated dyes A, B and C are shown on four tracks on the separation material (1); (2) marks the position of the eluant front. The original size of the separation material is about 14×56 mm; further experimental details are given in the description (Use Example A).

For the purposes of the present invention, the term support refers essentially to the supports customary in thin layer chromatography, for example plastic films or metal foils and in particular glass plates. However, owing to the miniaturization of the separation materials of the invention, it is in principle also possible to use other supports which have hitherto not been used in customary thin layer materials, for example for cost reasons; conceivable supports are silicon wafers or fused quartz.

The chromatographic separation takes place in the separation medium layer. In the prior art, the separation medium layer in separation materials for thin layer chromatography comprises, for example, particulate silica gel which may be modified by means of separation effectors and possibly further additives such as binders, fluorescent dyes or reflection reinforcers. The separation medium layers of the invention comprise silica gel which is produced in situ from polysilicic esters by hydrolysis and polymerization. The separation layers of the invention may further comprise customary additives; for example they can be modified by means of separation effectors or, for example, a fluorescence indicator can be incorporated into the separation medium layer.

The alcohol component of the polysilicic esters used according to the invention is derived from $C_1$–$C_5$-alcohols, in particular methanol, ethanol, n-propanol or i-propanol. The mean molecular weight of the polysilicic esters used according to the invention is in the range from 500 to 2000, preferably from 800 to 1500. Such polysilicic esters are commercially available. The polysilicic esters used according to the invention can be used as pure substances or as mixtures having various molecular weights and/or different alcohol components. It is also possible to dilute the polysilicic esters used according to the invention with suitable solvents; solvents which have been found to be particular useful are $C_1$–$C_5$-alcohols, for example methanol, ethanol, n-propanol or i-propanol. The solvent is preferably chosen so that the solvent and the alcohol component of the polysilicic ester are the same. The polysilicic ester content of the diluted solution should be at least 30% by weight.

The cleaning of the support is an important first process step. Here, the use of sodium hydroxide solution and detergents (e.g. Extran®) has been found to be useful; before the next step, the support is rinsed thoroughly with water.

The polysilicic ester subsequently has to be applied as a uniform liquid film to the support. Two methods have been found to be particularly useful for this purpose:

a) A sufficient liquid volume comprising the polysilicic ester is applied to the middle of the support; the support is subsequently rotated about the axis which runs through the point of application and is perpendicular to the plane of the support, so that a uniform liquid film is produced.

b) The polysilicic ester is sprayed in diluted or undiluted form onto the support.

Further methods are, for example: application by means of a technique similar to screen printing or by means of a roller.

The atmosphere in which the further hydrolysis and polymerization of the polysilicic ester takes place comprises water vapour together with either ammonia or hydrochloric acid. Such an atmosphere can be generated, for example, by introducing the support to which the liquid polysilicic ester has been applied into a chamber in which an open vessel of fuming hydrochloric acid is located and subsequently introducing hot steam into the chamber.

The polymerization of the polysilicic esters preferably takes place at from 15 to 80° C., in particular from 40 to 60° C., and takes from 3 minutes to 1 hour, depending on the temperature. After the polymerization and after the silica layer has been washed, the separation material is dried by customary methods at from 15 to 120° C. (depending on temperature, for from 5 to 30 minutes). The separation layers obtained according to the invention have a thickness of from 2 to 20 µm, in particular from 4 to 10 µm.

The mesopores formed in the process of the invention can be enlarged by customary methods, in particular by treatment with aqueous ammonia solution.

The silica gel layer on the support can additionally be modified using customary methods. For example, separation effectors such as ionic groups for ion-exchange chromatography or hydrophobic groups for reversed-phase chromatography can be introduced. Such modification methods and suitable separation effectors are known to those skilled in the art and are described in handbooks such as Packings and Stationary Phases in Chromatographic Techniques (K. K.: Unger ed.; Marcel Dekker, New York and Basel (1990)) or Porous Silica (K. K. Unger ed.; Elsevier, Amsterdam, Oxford New York (1979)). Particularly suitable modification methods for separation media for thin layer chromatography are those disclosed in DE 27 12 133 and DE 28 09 137.

Even without further explanations, a person skilled in the art will be able to make use of the above description in its widest scope. The preferred embodiments and examples are therefore to be regarded merely as descriptive and do not constitute any limitation.

The full disclosure of all patent applications, patents and publications mentioned above and below, and also the corresponding application DE 198 05 395.9, filed on Feb. 11, 1998, are incorporated by reference into the present application.

EXAMPLES

PRODUCTION EXAMPLES

Example 1

A 20×20 cm glass plate as is customary as support in thin layer chromatography is cleaned with sodium hydroxide solution and subsequently with Extran® and finally with water. About 0.8 ml of a 50% (v:v) ethanolic solution of polyethoxysilane (mean molecular weight about 1100) is subsequently sprayed on. The sprayed glass plate is introduced into a closed chamber in which an open vessel of fuming hydrochloric acid is located, hot steam (4 bar) is introduced and the glass plate is treated in this way for 30 minutes at 60° C. The coated glass plate is subsequently washed with water and dried. For use, the glass plate is cut into pieces of the desired size and shape.

The result is a separation material for thin layer chromatography whose separation medium layer consists of porous silica gel in a thickness of about 5 µm. The separation medium layer has a specific surface area of 410 $m^2$/g and a specific pore volume of about 0.32 ml/g (nitrogen adsorption by the BET method); this gives a mean pore size of 3 nm.

Example 2

A separation material produced as described in Example 1 is dipped into a solution of methyloctadecyl-dichlorosilane (10% by weight in toluene) for 5 minutes. The separation material is subsequently rinsed by dipping into various solvents: 5 minutes in toluene, 1 minute each in dichloromethane/methanol (1:1; v:v), in acetone/water (1:1; v:v) and in methanol. The plate is subsequently dried for 30 minutes at room temperature in the fume cupboard and for another 15 minutes at 120° C. in a drying oven.

This results in a $C_{18}$-modified separation material for reversed-phase chromatography.

Example 3

150 ml of fuming hydrochloric acid are placed in a conditioning chamber. The closed chamber is preheated to 60° C. (1 hour) in a drying oven. The chamber is taken from the drying oven and steam is introduced into the chamber (shut-off valve opened slightly for about 5 seconds).

A washed glass plate (10×20 cm) is cleaned with ethanol and dried. 400 µl of polyethoxysilane (mean molecular weight: 1000) are subsequently applied to the glass plate and drawn off using a 12 µm roller. The coated glass plate is placed on an expanded polystyrene plate (20×20 cm) in the conditioning chamber and heated at 60° C. for 30 minutes. The TLC plate is subsequently washed with water and dried in air.

The silica gel layer has a thickness of 12+1 µm and adheres firmly to the glass plate.

The silica gel layer can be modified as described in Example 2.

USE EXAMPLES

Use Example A

Separation of a Dye Mixture

Four spots of 50 nl each of a dye mixture comprising 0.1% by weight of violet I, 0.1% by weight of fast nitro blue 2B and 0.1% by weight of Sico oil-soluble blue 50401N dissolved in toluene are applied by means of a Hamilton syringe to a 14×56 mm TLC plate produced as described in Example 1. As eluant, use is made of toluene in a normal chamber (50 ml glass beaker with clock glass as cover) without chamber saturation. After an elution time of 1 minute, sufficient separation has been achieved; the elution distance is 8 mm.

FIG. 1 schematically shows the result of this experiment.

Use Example B

Chromatography of Cholesterol 50 nl of a solution of cholesterol (0.1% by weight in dichloromethane/methanol (1:1; v:v)) are applied by means of a Hamilton syringe to a 14×56 m TLC plate produced as described in Example 2 and the chromatogram is developed in acetone/water (95:5; v:v) (chamber saturation; elution distance: 7 mm; elution time: about 5 minutes). After the plate has been dried, it is sprayed with $MnCl_2$/sulfuric acid reagent and the colour is developed in a drying oven at 120° C. (5 minutes) An hRf value of 28.6 was found; this value indicates that the silica gel layer has been modified and the cholesterol is retained by the stationary phase.

What is claimed is:

1. Separation material for thin layer chromatography consisting of a support and a separation medium layer obtainable by the following process steps:
   a) cleaning of the support;
   b) application of a liquid film comprising a polysilicic ester to a support;
   c) introduction of the support with the liquid film into an atmosphere which effects hydrolysis and further polymerization of the polysilicic ester;
   d) hydrolysis and further polymerization of the polysilicic ester at constant temperature;
   e) washing of the silica layer;
   f) drying of the silica layer.

2. Separation material according to claim 1, further characterized by modification of the silica gel surface by means of separation effectors.

3. Process for producing a separation material for thin layer chromatography, which comprises the following steps:
   a) cleaning of the support;
   b) application of a liquid film comprising a polysilicic ester to a support;
   c) introduction of the support with the liquid film into an atmosphere which effects hydrolysis and further polymerization of the polysilicic ester;
   d) hydrolysis and further polymerization of the polysilicic ester at constant temperature;
   e) washing of the silica layer;
   f) drying of the silica layer.

4. Process according to claim 3, wherein the said liquid film is applied by spraying on.

5. Process according to claim 3, wherein the said liquid film is applied by firstly applying the liquid at one point and subsequently rotating the support about the point of application, with the axis of rotation being perpendicular to the plane of the support.

6. Process according to claim 3, wherein the said liquid film is applied by means of a roller.

7. A method of separating at least two substances by thin layer chromatography comprising applying the at least two materials to the separation materials of claim 1 and eluting the at least two substances.

* * * * *